United States Patent [19]
Wolf et al.

[11] 3,944,578
[45] Mar. 16, 1976

[54] ORGANIC SUPERCONDUCTORS WITH HIGH TRANSITION TEMPERATURES AND HIGH CRITICAL MAGNETIC FIELDS

[75] Inventors: Alfred A. Wolf; Ernest H. Halpern, both of Annapolis, Md.

[73] Assignee: The United States of America as represented by the Secretary of the Navy, Washington, D.C.

[22] Filed: Nov. 23, 1973

[21] Appl. No.: 418,337

[52] U.S. Cl. ............ 260/397.1; 252/108; 252/518; 260/478
[51] Int. Cl.² .......................................... C07J 9/00
[58] Field of Search ................................. 260/397.1

[56] References Cited
UNITED STATES PATENTS

| | | | |
|---|---|---|---|
| 2,429,899 | 10/1947 | Sondern et al. | 260/397.1 |
| 2,542,481 | 2/1951 | Crandall et al. | 260/397.1 |

*Primary Examiner*—Elbert L. Roberts
*Attorney, Agent, or Firm*—R. S. Sciascia; Q. E. Hodges; D. McGiehan

[57] ABSTRACT

Organic compounds exhibit superconducting-like behavior, as to magnetic and electrical properties, at elevated temperatures above 21°K, where 21°K is the transition temperature of most known metallic superconducting materials. The structure of the organic materials according to this invention is a plurality of superconducting clusters, forming islands within a matrix of insulating material. The ratio of the clusters to the matrix material is a minimum at $1:10^4$. The organic compound comprises two distinct atomic groups termed an R group and COOM group combining as R—COOM with the COOM group clustering to form superconducting islands, within the R material matrix.

15 Claims, 6 Drawing Figures

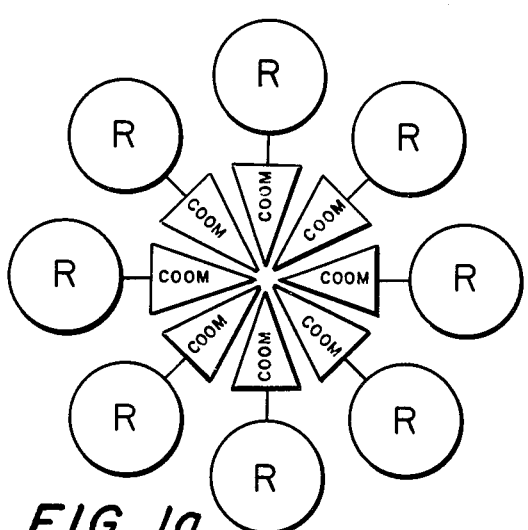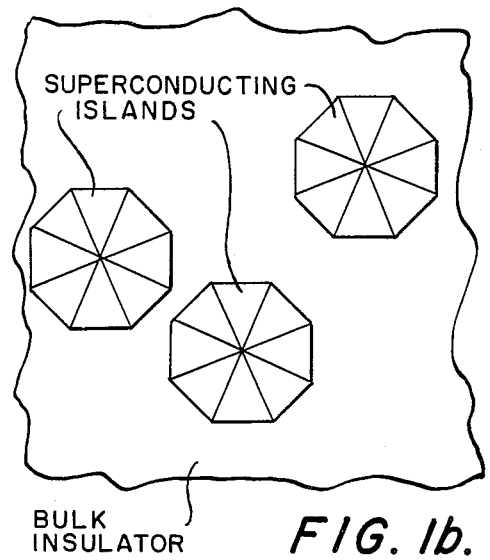
FIG. 1a.
FIG. 1b.
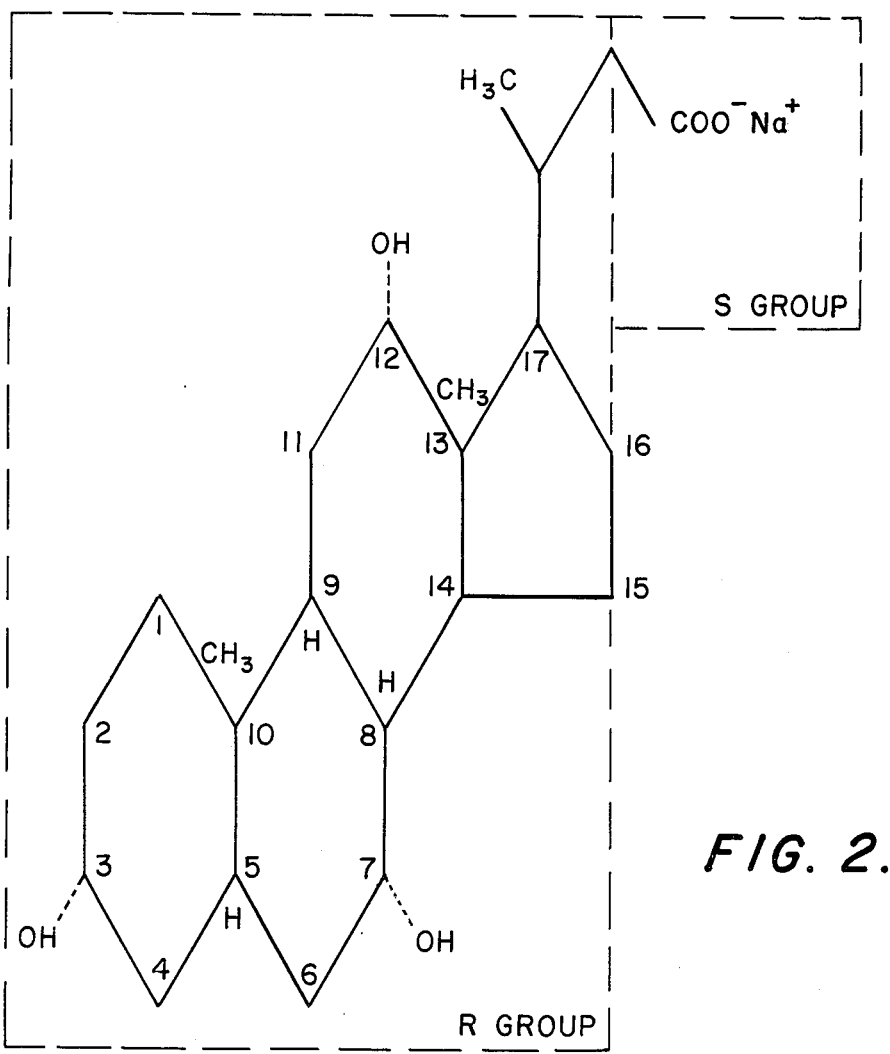
FIG. 2.

ORGANIC SUPERCONDUCTORS WITH HIGH TRANSITION TEMPERATURES AND HIGH CRITICAL MAGNETIC FIELDS

BACKGROUND OF THE INVENTION

Present superconductors have a transition temperature in the neighborhood of 21°K. While the advantages of the use of superconductors in some applications are well known, there are many disadvantages in their use. The disadvantages include the requirement of maintaining this material at extremely low temperatures, which requires elaborate refrigeration machinery and which contributes towards inefficiency of the application of superconductors to some apparatus. For example, the refrigeration power needed to compensate for the evaporation of liquid helium is between 500 to 1,000 watts for every watt of heat dissipation of the liquid helium.

SUMMARY OF THE INVENTION

This invention relates to materials and methods of making materials which have superconducting transition temperatures above 21°K. The advantages of the use of such materials is that less refrigeration power is needed to maintain the higher superconducting temperature of these materials, and therefore the efficiency of use of these materials is thereby increased.

The structure of these materials is substantially that of an insulator with superconducting-like clusters that form islands throughout the bulk of the material, in an approximate ratio of $1:10^4$. These materials can be considered fractional superconductors because the islands are merely superconducting clusters dispersed randomly in the bulk insulating matrix.

As such, these materials have application in electronics such as in very high Q circuits, in extremely wide band wave guides, in electrical machinery, in magnets hydrodynamic systems, and in fusion systems. They also can be used to make superconducting components, such as ultra-wide band data transmission systems, superconducting switches, superconducting energy storage devices, and for other uses in the areas of radio, radar microwave elements, and navigational systems.

DISCLOSURE OF THE INVENTION

A schematic construction of the organic superconducting compound R-COOM according to this invention is shown as

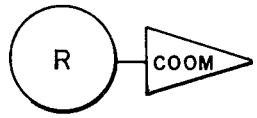

The selection of the R group of atoms controls the transition temperature of the compound, whereas the COOM group of atoms control the intensity of superconductivity or superconducting quality. Superconductivity is achieved when the molecules are so oriented that the COOM group atoms are arranged in a cluster achieving a minimum critical mass, and the R group atoms surrounding their respective COOM atoms forming the bulk matrix, as shown in FIG. 1a or FIG. 1b.

Within the meaning of this invention the superconducting materials have the general formula $(RCOO^-)_x M^x$ wherein R is selected from the group consisting of a metal, an aliphatic organic radical, cyclic organic radical, and aromatic organic radical and a heterocyclic organic radical. M is a cation which may either be singly charged e.g. $H^+$, $Na^+$ etc) or multiply charged and $x$ is the valence of M. In this regard it should be noted that $x$ is preferably 1, M is preferably H or a metal cation, and most preferably an alkali metal cation (particularly Na) and R is preferably a derivative of cholic acid (a cyclic organic radical) or a metal such as Li or Cu.

DESCRIPTION OF THE PREFERRED EMBODIMENT

The superconducting materials of the present invention are of the formula $(RCOO^-)_x M^x$ wherein R is selected from the group consisting of a metal, a cyclic organic radical, an aliphatic organic radical, an aromatic organic radical and a heterocyclic organic radical; M is a cation which may be singly or multiply charged and $x$ is the valence of M.

Particularly good materials of the above formula are materials wherein R is a cyclic organic radical and particularly wherein R is a cholic acid derivative.

The $(COO)_x M^x$ portion of the superconductors of this invention are derived from the carboxyl group. Although it is preferred that M be singly charged it can also be multiply charged. Among the preferred materials of M are hydrogen and metal cations, with H and alkali metal cations being preferred, H and Na being the most preferred materials. When M is multiply charged, it is preferably calcium or magnesium.

Figure 4:
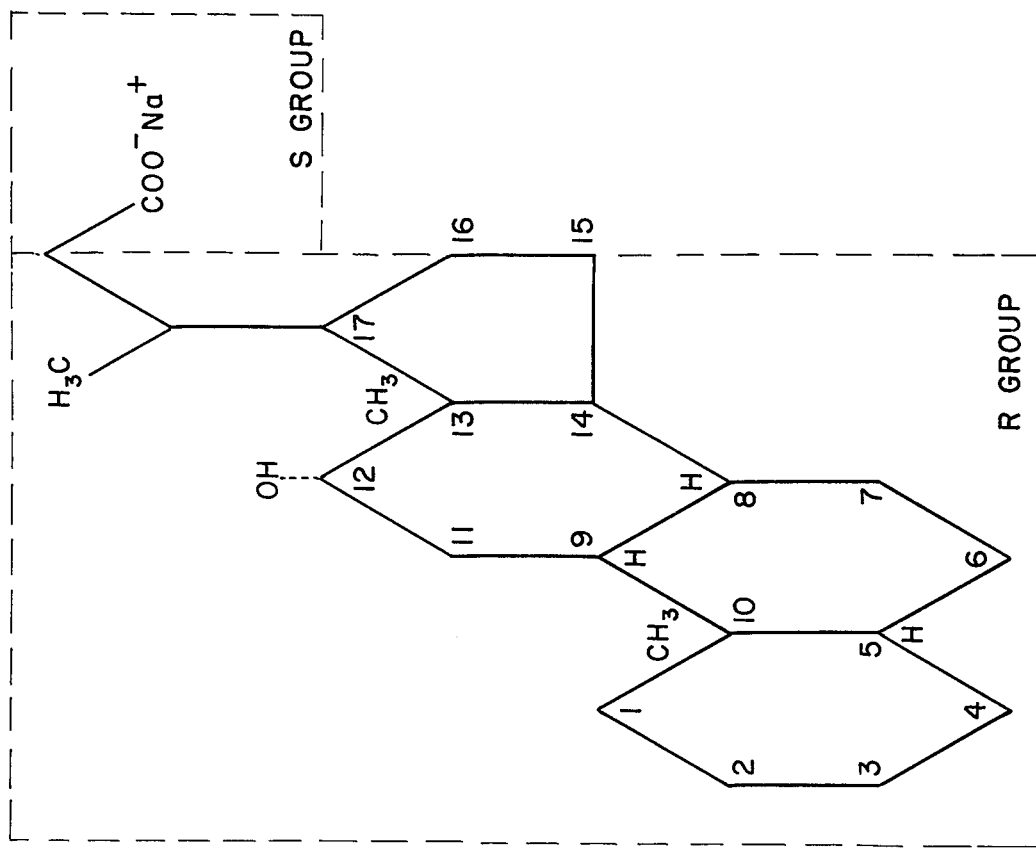
Figure 3:
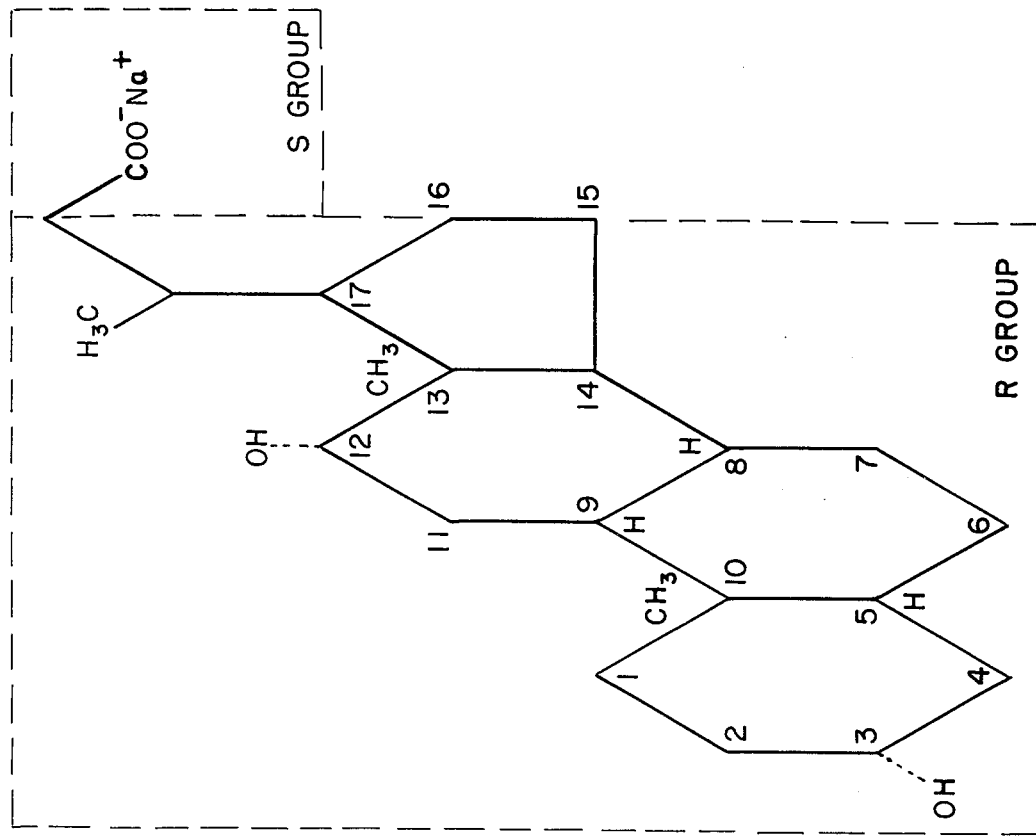
Figure 5:
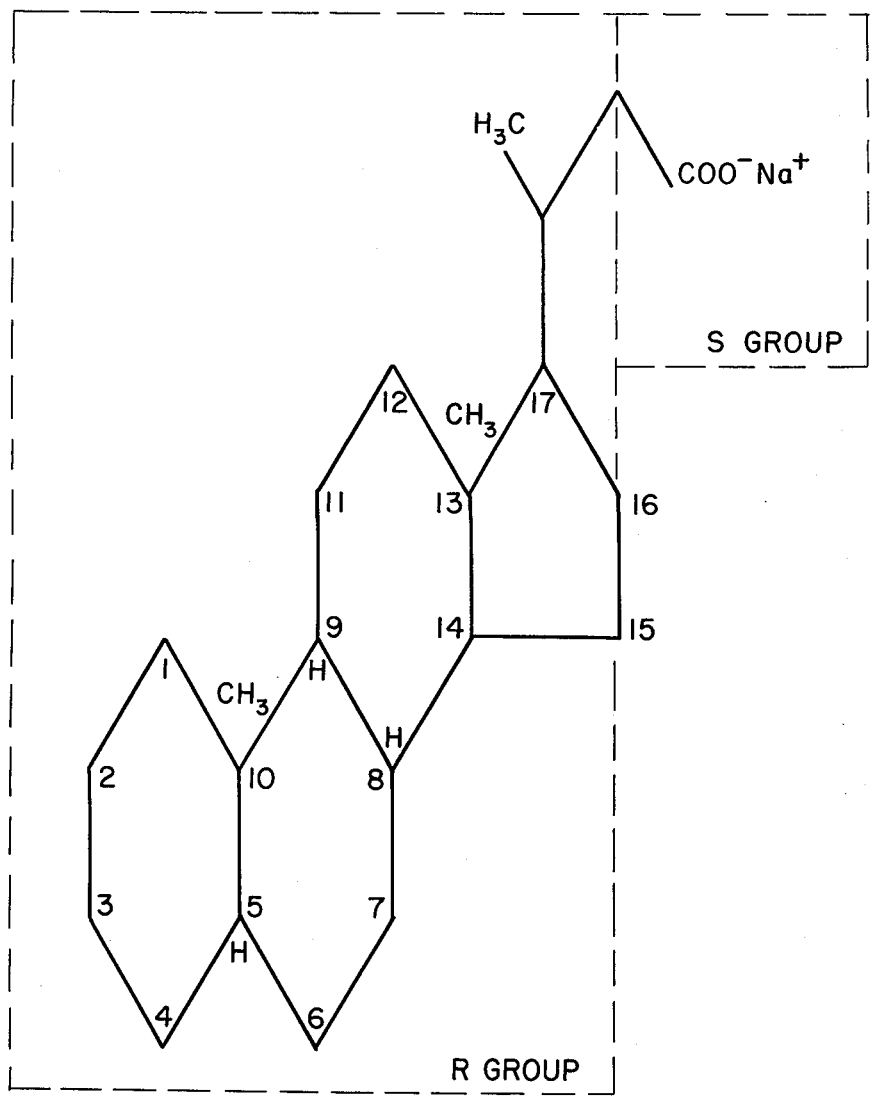

The method of producing these cholanate superconducting compounds simply requires the reaction of a material having at least a double covalent bond such as carboxylic acid or carboxylic salt with an organic acid. In the case of the specific compounds in FIGS. 2 to 5, sodium hydroxide is reacted with an acid, having the appropriate cholanate group to form one of the respective compounds shown.

Another preferred series of compounds of the formula $(RCOO^-)_x M^x$ are those wherein R is a metal and particularly where R is either Li or Cu. Thus the compound copper sodium formate having the structure

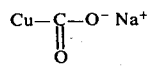

and lithium sodium formate having the structure

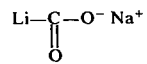

are particularly preferred. These compounds may be formed by the following reaction sequences.

Copper Sodium Formate

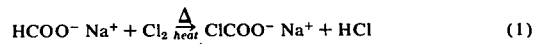

Lithium Sodium Formate

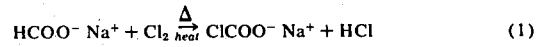

$$\text{LiH} + \text{ClCOO}^- \text{Na}^+ \xrightarrow[\text{heat}]{\Delta} \text{LiCOO}^- \text{Na}^+ + \text{HCl} \quad (2)$$

These compounds are prepared as follows:

EXAMPLE I

COPPER SODIUM FORMATE: 1.2 moles of sodium formate is first chlorinated by passing chlorine gas through a sodium formate suspension using antimony chloride as a catalyst. 0.1% of the sodium formate, under the application of heat, in the reaction zone forms chlorosodium formate which is precipitated out and filtered. This chlorosodium formate is then reacted on a mole-to-mole basis with copper hydride in a glass distillation set-up with the application of heat using a heating mantel. The resulting hydrogen chloride is vented through a glass column in the reaction vessel. The residual copper sodium formate and copper hydride is alcohol and water washed, thus separating the copper sodium formate. The solvent is evaporated slowly under vacuum to achieve proper orientation of the molecules.

EXAMPLE II

LITHIUM SODIUM FORMATE: 1.2 moles of sodium formate is first chlorinated by passing chlorine gas through a sodium formate suspension using antimony chloride as a catalyst. 0.1% of the sodium formate, under the application of heat in the reaction zone forms chlorosodium formate which is precipitated out and filtered. This chlorosodium formate is then reacted on a mole-to-mole basis with lithium hydride in a glass distillation set-up with the application of heat using a heating mantel. The resulting hydrogen chloride is vented through a glass column in the reaction vessel. The residual lithium sodium formate and copper hydride is alcohol and water washed, thus removing the lithium sodium formate. The solvent is then evaporated slowly under vacuum to achieve proper orientation of the molecules.

It should be noted that better results have been achieved when R is a metal rather than when R is some type of organic radical.

The method of forming the COOM clusters and the surrounding matrix of the R part of each respective molecule such as the cholanates shown in FIGS. 2–5 and the metallic compounds shown above and described by the chemical formula, is well know in the art. However, these compounds will not be superconducting when originally formed. To make them superconducting, it is necessary to arrange or orient the COOM parts of each compound in a cluster, and to make the R part of each respective part, surround the cluster to thus form the matrix as shown in FIGS. 1a and 1b. This is accomplished by first forming the compound, in solution or in a liquid state. In solution, the COOM parts will form clusters, but they will be an unstable structure not capable of superconductivity. It is thus necessary to convert the solution to a solid state while retaining the orientation or arrangement of the COOM clusters as shown in FIG. 1b. This is accomplished by desiccating the compound formed in solution or evaporating the solvent in a vacuum.

The orientation of COOM clusters is possible in water when the atomic structure of the COOM part is hydrophilic while the atomic structure of the R part is hydrophobic. Separating and clustering of the R and COOM parts is due to the affinity of the COOM part for water, and the self exclusion of the R part from water. In water solution, this hydrophobic-hydrophilic combination causes the orientation of clusters as described above. It is then necessary to remove the water by dessication or evaporation to solidify the R—COOM molecule in the proper orientation to give the compound its superconductive property. Thus the additional limitation imposed upon these superconducting R—COOM molecules is that one part, either the R or COOM part be hydrophobic and the other respective part be hydrophilic. Under this condition, the water solution will force the COOM parts of each molecule to cluster and form the superconducting islands and the R parts to disperse and form the surrounding matrix.

Of course when other solvents are utilized, a similar condition must exist in order to form the necessary grouping of the molecules.

What is claimed is:

1. A method of preparing a superconductive material of the formula $(\text{RCOO}^-)_x \text{M}^x$, wherein R is selected from the group consisting of a metal, a cyclic organic radical, an aliphatic organic radical, an aromatic organic radical, and a heterocyclic organic radical; M is a cation; and $x$ is the valence of M, comprising the steps of:

preparing a water solution of the material at room temperature;
   establishing a vacuum over said solution; and
   evaporating slowly the solvent to cause the constituent molecules to orient with the COOM group in clusters surrounded by a matrix of the R group.

2. A superconducting material produced by the steps of:

passing chlorine gas through a sodium formate suspension;
   using antimony chloride as a catalyst;
   applying heat in the reaction zone to form chlorosodium formate;
   precipitating said chlorosodium formate;
   filtering said chlorosodium formate from the other constituents;
   reacting said precipitated and filtered chlorosodium formate on a mole-to-mole with copper hydride with the application of heat;
   distilling the resulting copper sodium formate having the general formula R—COOM, wherein R is the copper and COOM is the sodium formate, and the remaining copper hydride to remove hydrogen chloride;
   washing with water and alcohol the residual copper sodium formate and copper hydride to dissolve and separate out the copper sodium formate; and
   evaporating slowly the solvent containing said copper sodium formate to achieve orientation of the molecules to achieve clustering of the superconducting COOM portion of the molecule with a surrounding matrix of the R portion.

3. The superconducting material produced by claim 2 wherein:

lithium hydride replaces said copper hydride in the reacting step to produce lithium sodium formate.

4. The method of making a superconducting material produced by claim 2 wherein:

said superconducting COOM portion is hyrophillic: and said R portion is hydrophobic.

5. The superconducting material produced by claim 3 wherein:

said superconducting COOM portion is hydrophillic: and said R portion is hydrophobic.

6. The method of preparing the superconductive material of claim 1 wherein x is equal to 1.

7. The method of preparing the superconductive material of claim 6 wherein M is selected from the group consisting of hydrogen (H) and an alkali metal.

8. The method of preparing the superconductive material of claim 7 wherein M is selected from the group consisting of hydrogen (H) and sodium (Na).

9. The method of preparing the superconductive of claim 1 wherein R is a metal.

10. The method of preparing the superconductive material of claim 9 wherein x is 1.

11. The method of preparing the superconductive material of claim 9 wherein M is selected from the group consisting of hydrogen (H) and an alkali metal.

12. The method of preparing the superconductive material of claim 11 wherein M is selected from the group consisting of hydrogen (H) and Sodium (Na).

13. The method of preparing the superconductive material of claim 1 wherein R is a cyclic organic radical.

14. The method of preparing the superconductive material of claim 13 wherein said cyclic organic radical is a cholic acid derivitive.

15. The method of preparing the superconductive material of claim 14 wherein said cholic acid derivitive is selected from the group consisting of a cholate salt, a desoxycholate salt, a lithocholate salt, and a cholanate salt.

* * * * *